(12) United States Patent
Dubson et al.

(10) Patent No.: US 7,276,271 B2
(45) Date of Patent: Oct. 2, 2007

(54) POLYMER FIBER TUBULAR STRUCTURE HAVING KINKING RESISTANCE

(75) Inventors: Alexander Dubson, Hadera (IL); Eli Bar, Moshav Megadim (IL)

(73) Assignee: Nicast Ltd., Lod (IL)

( * ) Notice: Subject to any disclaimer, the term of this patent is extended or adjusted under 35 U.S.C. 154(b) by 357 days.

(21) Appl. No.: 10/471,276

(22) PCT Filed: Mar. 19, 2002

(86) PCT No.: PCT/IL02/00219

§ 371 (c)(1),
(2), (4) Date: Sep. 17, 2003

(87) PCT Pub. No.: WO02/074190

PCT Pub. Date: Sep. 26, 2002

(65) Prior Publication Data

US 2004/0096532 A1    May 20, 2004

Related U.S. Application Data

(60) Provisional application No. 60/276,956, filed on Mar. 20, 2001.

(30) Foreign Application Priority Data

Dec. 19, 2000  (US)  .................. 60256323
Mar. 20, 2001  (US)  .................. 60/276956
Oct. 19, 2001  (US)  .................. 09/982017

(51) Int. Cl.
*B29D 22/00* (2006.01)
*B32B 1/08* (2006.01)

(52) U.S. Cl. .............. 428/36.9; 264/10; 264/441; 264/484; 425/174.8 E; 425/174.8 R; 427/2.25; 427/458; 427/478; 427/483; 428/34.1; 428/36.4; 428/36.91

(58) Field of Classification Search ............... 428/36.4, 428/34.1, 36.9, 36.91; 425/174.8 E, 174.8 R; 264/10, 484, 441; 427/2.25, 458, 478, 483
See application file for complete search history.

(56) References Cited

U.S. PATENT DOCUMENTS

| | | | |
|---|---|---|---|
| 2,491,889 A | 12/1949 | Bennett et al. | |
| 3,280,229 A | 10/1966 | Simons | |
| 3,425,418 A | 2/1969 | Chvapil et al. | |
| 3,625,745 A | 12/1971 | Wright et al. | |
| 3,688,317 A | 9/1972 | Kurtz | |
| 3,860,369 A * | 1/1975 | Brethauer et al. | ............. 425/3 |
| 4,044,404 A | 8/1977 | Martin et al. | |
| 4,223,101 A | 9/1980 | Fine et al. | |

(Continued)

FOREIGN PATENT DOCUMENTS

EP     0223374     5/1987

(Continued)

*Primary Examiner*—Nasser Ahmad

(57) ABSTRACT

An apparatus for forming a tubular structure from a liquefied polymer, the apparatus comprising: (a) a dispenser for dispensing the liquefied polymer; (b) a precipitation electrode being at a first potential relative to the dispenser, the precipitation electrode being designed and constructed for generating a polymeric shell thereupon; and (c) a mechanism for increasing a local density of the polymeric shell in a plurality of predetermined sub-regions of the polymeric shell, thereby to provide a tubular structure having an alternating density in a longitudinal direction.

37 Claims, 4 Drawing Sheets

U.S. PATENT DOCUMENTS

| | | | |
|---|---|---|---|
| 4,323,525 | A | 4/1982 | Bornat |
| 4,345,414 | A | 8/1982 | Bornat et al. |
| 4,368,277 | A | 1/1983 | Burinsky et al. |
| 4,475,972 | A | 10/1984 | Wong |
| 4,524,036 | A | 6/1985 | Gilding et al. |
| 4,657,793 | A | 4/1987 | Fisher |
| 4,689,186 | A * | 8/1987 | Bornat ............... 264/6 |
| 4,738,740 | A | 4/1988 | Pinchuk et al. |
| 4,739,013 | A | 4/1988 | Pinchuk |
| 4,743,252 | A | 5/1988 | Martin, Jr. et al. |
| 4,759,757 | A | 7/1988 | Pinchuk |
| 4,769,030 | A | 9/1988 | Pinchuk |
| 4,798,606 | A | 1/1989 | Pinchuk |
| 4,842,505 | A | 6/1989 | Annis et al. |
| 4,872,455 | A | 10/1989 | Pinchuk et al. |
| 4,878,908 | A | 11/1989 | Martin et al. |
| 4,880,002 | A | 11/1989 | MacGregor |
| 4,904,174 | A | 2/1990 | Moosmayer et al. |
| 4,905,367 | A | 3/1990 | Pinchuk et al. |
| 4,965,110 | A | 10/1990 | Berry |
| 4,990,158 | A | 2/1991 | Kaplan et al. |
| 4,997,600 | A | 3/1991 | Okumura et al. |
| 5,019,090 | A | 5/1991 | Pinchuk |
| 5,024,671 | A | 6/1991 | Tu et al. |
| 5,024,789 | A | 6/1991 | Berry |
| 5,084,065 | A | 1/1992 | Weldon et al. |
| 5,092,877 | A | 3/1992 | Pinchuk |
| 5,116,360 | A | 5/1992 | Pinchuk et al. |
| 5,133,742 | A | 7/1992 | Pinchuk |
| 5,147,725 | A | 9/1992 | Pinchuk |
| 5,226,913 | A | 7/1993 | Pinchuk |
| 5,298,255 | A | 3/1994 | Sawamoto et al. |
| 5,334,201 | A | 8/1994 | Cowan |
| 5,360,397 | A | 11/1994 | Pinchuk |
| 5,376,117 | A | 12/1994 | Pinchuk et al. |
| 5,383,922 | A | 1/1995 | Zipes et al. |
| 5,383,928 | A | 1/1995 | Scott et al. |
| 5,415,664 | A | 5/1995 | Pinchuk |
| 5,419,760 | A | 5/1995 | Narciso, Jr. |
| 5,545,208 | A | 8/1996 | Wolff et al. |
| 5,549,663 | A | 8/1996 | Cottone, Jr. |
| 5,554,722 | A | 9/1996 | Eichenauer et al. |
| 5,558,809 | A | 9/1996 | Groh et al. |
| 5,575,818 | A | 11/1996 | Pinchuk |
| 5,591,227 | A | 1/1997 | Dinh et al. |
| 5,609,629 | A | 3/1997 | Fearnot et al. |
| 5,624,411 | A | 4/1997 | Tuch |
| 5,628,788 | A | 5/1997 | Pinchuk |
| 5,632,772 | A | 5/1997 | Alcime et al. |
| 5,637,113 | A | 6/1997 | Tartaglia et al. |
| 5,639,278 | A | 6/1997 | Dereume et al. |
| 5,653,747 | A | 8/1997 | Dereume |
| 5,697,967 | A | 12/1997 | Dinh et al. |
| 5,700,269 | A | 12/1997 | Pinchuk et al. |
| 5,723,004 | A | 3/1998 | Dereume et al. |
| 5,725,567 | A | 3/1998 | Wolff et al. |
| 5,726,107 | A | 3/1998 | Dahringer et al. |
| 5,733,327 | A | 3/1998 | Igaki et al. |
| 5,741,333 | A | 4/1998 | Frid |
| 5,749,921 | A | 5/1998 | Lenker et al. |
| 5,755,722 | A | 5/1998 | Barry et al. |
| 5,755,774 | A | 5/1998 | Pinchuk |
| 5,766,710 | A | 6/1998 | Turnlund et al. |
| 5,797,887 | A | 8/1998 | Rosen et al. |
| 5,824,048 | A | 10/1998 | Tuch |
| 5,824,049 | A | 10/1998 | Ragheb et al. |
| 5,837,008 | A | 11/1998 | Berg et al. |
| 5,843,172 | A | 12/1998 | Yan |
| 5,849,037 | A | 12/1998 | Frid |
| 5,855,598 | A | 1/1999 | Pinchuk |
| 5,871,538 | A | 2/1999 | Dereume |
| 5,900,246 | A | 5/1999 | Lambert |
| 5,928,247 | A | 7/1999 | Barry et al. |
| 5,938,697 | A | 8/1999 | Killion et al. |
| 5,948,018 | A | 9/1999 | Dereume et al. |
| 5,968,070 | A | 10/1999 | Bley et al. |
| 5,968,091 | A | 10/1999 | Pinchuk et al. |
| 5,980,551 | A | 11/1999 | Summers et al. |
| 5,980,972 | A | 11/1999 | Ding |
| 6,001,125 | A | 12/1999 | Golds et al. |
| 6,004,346 | A | 12/1999 | Wolff et al. |
| 6,013,099 | A | 1/2000 | Dinh et al. |
| 6,017,362 | A | 1/2000 | Lau |
| 6,019,789 | A | 2/2000 | Dinh et al. |
| 6,102,939 | A | 8/2000 | Pinchuk |
| 6,106,913 | A | 8/2000 | Scardino et al. |
| 6,117,425 | A | 9/2000 | MacPhee et al. |
| 6,165,212 | A | 12/2000 | Dereume et al. |
| 6,252,129 | B1 | 6/2001 | Coffee |
| 6,265,333 | B1 | 7/2001 | Dzenis et al. |
| 6,270,793 | B1 | 8/2001 | Van Dyke et al. |
| 6,306,424 | B1 | 10/2001 | Vyakarnam et al. |
| 6,308,509 | B1 | 10/2001 | Scardino et al. |
| 6,309,413 | B1 | 10/2001 | Dereume et al. |
| 6,604,925 | B1 | 8/2003 | Dubson |
| 2001/0020652 | A1 | 9/2001 | Kadlubowski et al. |
| 2002/0002395 | A1 | 1/2002 | Berg et al. |
| 2002/0081732 | A1 | 6/2002 | Bowlin et al. |
| 2003/0191519 | A1 | 10/2003 | Lombardi et al. |
| 2004/0053553 | A1 | 3/2004 | Dubson et al. |

FOREIGN PATENT DOCUMENTS

| | | |
|---|---|---|
| EP | 0253539 | 1/1988 |
| EP | 0523960 | 1/1993 |
| GB | 2142870 | 1/1985 |
| WO | WO 01/54667 | 2/2001 |
| WO | WO 01/66035 | 9/2001 |
| WO | WO 02/40242 | 5/2002 |
| WO | WO 02/49535 | 6/2002 |
| WO | WO 02/49536 | 6/2002 |
| WO | WO 02/49678 | 6/2002 |
| WO | WO 02/074189 | 9/2002 |
| WO | WO 02/074191 | 9/2002 |
| WO | WO 2005/065578 | 7/2005 |

* cited by examiner

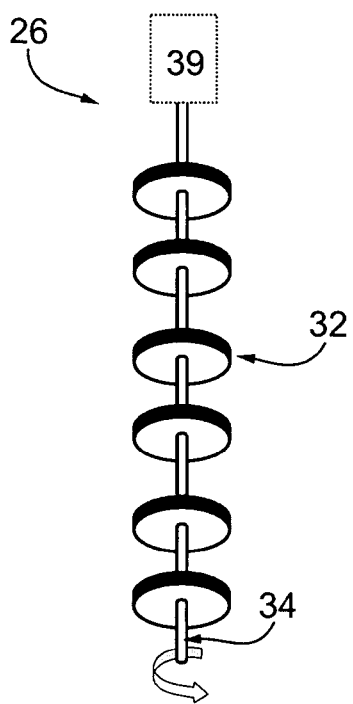
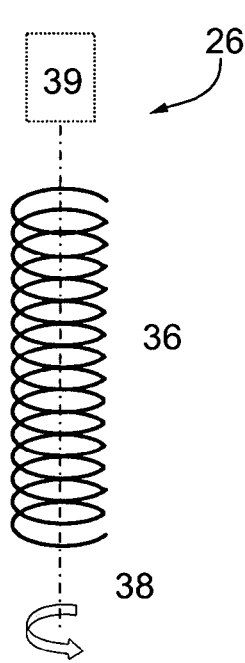
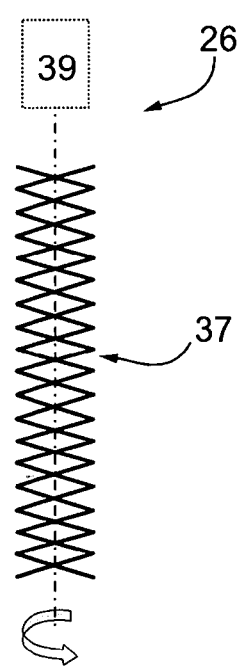
Fig. 3a    Fig. 3b    Fig. 3c
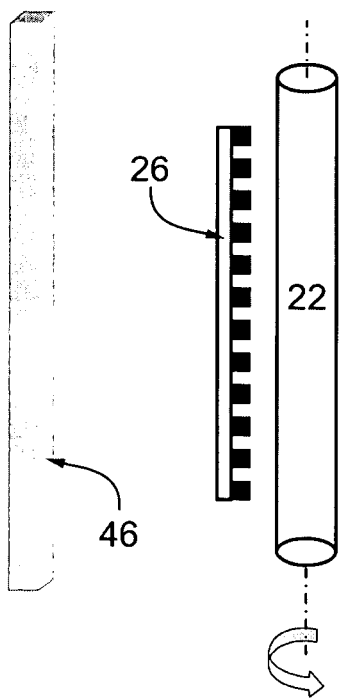
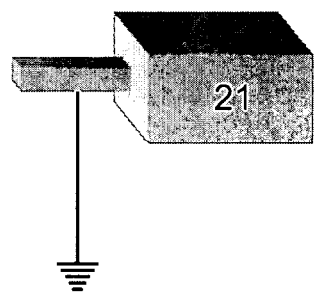
Fig. 4

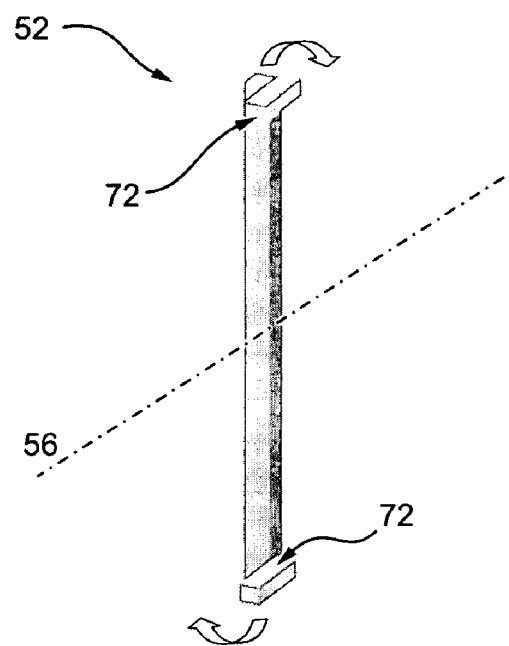
Fig. 7
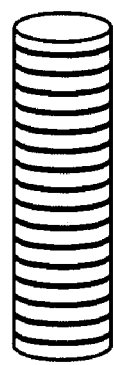  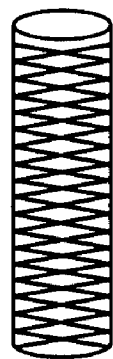
Fig. 8a          Fig. 8b          Fig. 8c

POLYMER FIBER TUBULAR STRUCTURE HAVING KINKING RESISTANCE

RELATED PATENT APPLICATION

This application is a National Phase Application of PCT/IL02/00219 International Filing Date 19 Mar. 2002, which claims priority from U.S. patent application Ser. No. 09/982,017 filed 19 Oct. 2001, now abandoned, which claims priority from U.S. Provisional Patent Application No. 60/276,956 filed 20 Mar. 2001 and U.S. Provisional Patent Application No. 60/256,323 filed on Dec. 19, 2000.

FIELD AND BACKGROUND OF THE INVENTION

The present invention relates to a method and apparatus for manufacturing tubular structures via electrospinning and, more particularly, to a method and apparatus for manufacturing a polymer fiber tubular structure having improved kinking resistance. The present invention further relates to tubular structures having improved kinking resistance.

In many medical and industrial applications, tubular structures made from polymer fibers are used as, e.g., vascular prostheses, shunts and the like. Production of polymer fiber tubular structures is particularly difficult when such tubular structures are required to have radial tensile strength sufficient to resist tearing and collapse in response to a pulsating pressure while at the same time maintain several elastic properties, such as the ability to bend without breaking and without kinking, in order to allow conformation to a complex geometry.

When an elastic tubular product bends, it experience a finite force onto a small surface area, hence the stress concentration at the bending point is high. Consequently, the tubular product is kinked, i.e., it either undergoes destruction, or bends with inner lumen collapse.

A typical method known in the art to prevent such a collapse is to support the surfaces of the tubular product by rigid circular members so that the product is made of alternating elastic and rigid longitudinal sections. Upon axial deformations, the elastic members can freely operate by tension-compression within the limits admissible by the agent elastic properties, while at the same time, development of radial deformations is limited by the presence of the rigid elements.

Radial support of tubular product can be done in more than one way. For example, tube corrugation provides alternating sections with differing diameter but permanent wall thickness. In this case, required rigidity is achieved at the expense of a plurality of wall members oriented at an angle which is close to 90° relative to the tube central axis. Another method is to reinforce an inner or outer wall of an elastic tube, by a rigid spiral pattern made of steel wire or polymer thread of an appropriate diameter. This type of structure can be also found in physiological systems such as the tracheal and the bronchial of the respiratory system, were rigid cartilage-tissue rings are interconnected by the elastic connective tissue.

In the vascular system, blood vessels possess integrity of unique biomechanical properties. Of particular importance is the resistance of the vessel to inner lumen collapse upon sharp "corners", which ensures normal blood supply.

Production of tubular fibrous products, including artificial blood vessels, is described in various patents inter alia using the technique of electrospinning of liquefied polymer, so that tubular products comprising polymer fibers are obtained.

Electrospinning is a method for the manufacture of ultra-thin synthetic fibers, which reduces the number of technological operations and increases the stability of properties of the product being manufactured.

The process of electrospinning creates a fine stream or jet of liquid that upon proper evaporation of a solvent or liquid to solid transition state yield a non-woven structure. The fine stream of liquid is produced by pulling a small amount of polymer solution through space via electrical forces. More particularly, the electrospinning process involves the subjection of a liquefied polymer substance into an electric field, whereby the liquid is caused to produce fibers that are drawn by electric forces to an electrode, and are, in addition, subjected to a hardening procedure. In the case of liquid which is normally solid at room temperature, the hardening procedure may be mere cooling; however other procedures such as chemical hardening (polymerization) or evaporation of solvent may also be employed. The produced fibers are collected on a suitably located sedimentation device and subsequently stripped of it.

Artificial vessels made by electrospinning have a number of vital characteristics, including the unique fiber microstructure, in many ways similar to that of the natural muscular tissue, high radial compliance and good endothelization ability. However, an artificial vessel fabricated using conventional electrospinning does not withstand kinking, and further reinforcement of the final product is necessary.

The inner surface of blood vessel prosthesis must be completely smooth and even so as to prevent turbulence during blood flow and related thrombogenesis. This feature prevents the employment of tube corrugation, since such structure affects the blood flow and may cause thrombogenesis. In addition, the vessel rigid members must ensure radial compliance and, if possible, have fiber structure and porosity similar to that of the basic material of the prosthesis wall. Still in addition, the rigid members should under no conditions be separated from the elastic portions of the prosthesis. On the other hand, in the vascular system, application of various adhesives is highly undesirable. Hence, the above mentioned techniques, to prevent collapse of the vessel lumen are inapplicable.

There is thus a widely recognized need for, and it would be highly advantageous to have, a method and apparatus for manufacturing tubular structures, and particularly vascular prostheses, devoid of the above limitations.

SUMMARY OF THE INVENTION

According to one aspect of the present invention there is provided an apparatus for forming a tubular structure from a liquefied polymer, the apparatus comprising: (a) a dispenser for dispensing the liquefied polymer; (b) a precipitation electrode being at a first potential relative to the dispenser, the precipitation electrode being designed and constructed for generating a polymeric shell thereupon; and (c) a mechanism for increasing a local density of the polymeric shell in a plurality of predetermined sub-regions of the polymeric shell, thereby to provide a tubular structure having an alternating density in a longitudinal direction.

According to further features in preferred embodiments of the invention described below the mechanism for increasing the local density comprises a pressing mechanism.

According to still further features in the described preferred embodiments the mechanism for increasing the local density comprises a plurality of rollers spaced apart from one another.

According to still further features in the described preferred embodiments the mechanism for increasing the local density comprises a spiral pattern.

According to still further features in the described preferred embodiments the mechanism for increasing the local density comprises a rigid irregular pattern.

According to still further features in the described preferred embodiments the dispenser is operable to move along the precipitation electrode.

According to still further features in the described preferred embodiments the apparatus further comprising a reservoir for holding the liquefied polymer.

According to still further features in the described preferred embodiments the apparatus further comprising a subsidiary electrode being at a second potential relative to the dispenser, and being for modifying an electric field generated between the precipitation electrode and the dispenser.

According to still further features in the described preferred embodiments the subsidiary electrode serves for reducing non-uniformities in the electric field.

According to still further features in the described preferred embodiments the subsidiary electrode serves for controlling fiber orientation of the tubular structure formed upon the precipitation electrode.

According to still further features in the described preferred embodiments the subsidiary electrode is operative to move along the precipitation electrode.

According to still further features in the described preferred embodiments the subsidiary electrode is tilted at angle with respect to the precipitation electrode.

According to still further features in the described preferred embodiments the apparatus further comprising a mechanism for intertwining at least a portion of a plurality of polymer fibers dispensed by the dispenser, so as to provide at least one polymer fiber bundle moving in a direction of the precipitation electrode.

According to still further features in the described preferred embodiments the mechanism for intertwining at least a portion of the plurality of polymer fibers comprises a system of electrodes, being laterally displaced from the dispenser, being at a third potential relative to the dispenser and capable of providing an electric field having at least one rotating component around a first axis defined between the dispenser and the precipitation electrode.

According to still further features in the described preferred embodiments the system of electrodes includes at least one rotating electrode, operable to rotate around the first axis.

According to still further features in the described preferred embodiments the dispenser and the at least one rotating electrode are operative to independently move along the precipitation electrode.

According to still further features in the described preferred embodiments the dispenser and the at least one rotating electrode are operative to synchronically move along the precipitation electrode.

According to another aspect of the present invention there is provided a method of forming a tubular structure from a liquefied polymer, the method comprising: (a) via electrospinning, dispensing the liquefied polymer from a dispenser in a direction of a precipitation electrode, hence forming polymeric shell; and (b) increasing a local density of the polymeric shell in a plurality of predetermined sub-regions of the polymeric shell, thereby providing a tubular structure having an alternating density in a longitudinal direction.

According to further features in preferred embodiments of the invention described below, the method further comprising independently repeating the steps (a) and (b) at least once.

According to still further features in the described preferred embodiments increasing the local density is done by applying pressure onto the predetermined sub-regions of the polymeric shell.

According to still further features in the described preferred embodiments increasing the local density is done by pressing a plurality of rollers, spaced apart from one another, onto the polymeric shell.

According to still further features in the described preferred embodiments increasing the local density is done by pressing a spiral pattern onto the polymeric shell.

According to still further features in the described preferred embodiments increasing said local density is done by pressing a rigid irregular pattern onto said polymeric shell.

According to still further features in the described preferred embodiments the method further comprising mixing the liquefied polymer with a charge control agent prior to the step of dispensing.

According to still further features in the described preferred embodiments the method further comprising reducing non-uniformities in an electric field generated between the precipitation electrode and the dispenser.

According to still further features in the described preferred embodiments reducing non-uniformities in the electric field is done by positioning a subsidiary electrode, being at a second potential relative to the precipitation electrode, close to the precipitation electrode.

According to still further features in the described preferred embodiments the method further comprising controlling fiber orientation of the tubular structure formed upon the precipitation electrode.

According to still further features in the described preferred embodiments controlling fiber orientation is done by positioning a subsidiary electrode, being at a second potential relative to the precipitation electrode, close to the precipitation electrode.

According to still further features in the described preferred embodiments the method further comprising moving the subsidiary electrode along the precipitation electrode.

According to still further features in the described preferred embodiments the method further comprising tilting the subsidiary electrode at angle with respect to the precipitation electrode.

According to still further features in the described preferred embodiments the method further comprising entangling at least a portion of a plurality of polymer fibers dispensed by the dispenser, so as to provide at least one polymer fiber bundle moving in a direction of the precipitation electrode.

According to still further features in the described preferred embodiments the step of entangling comprises providing an electric field having at least one rotating component around a first axis defined between the precipitation electrode and the dispenser.

According to still further features in the described preferred embodiments providing an electric field having at least one rotating component, is done by providing a system of electrodes, being laterally displaced from the dispenser, being at a third potential relative to the precipitation electrode and operable to provide a time-dependent electric field.

According to still further features in the described preferred embodiments providing an electric field having at least one rotating component, is done by providing at one rotating electrode, being laterally displaced from the dispenser, being at a third potential relative to the precipitation electrode and operable to rotate around the first axis.

According to still further features in the described preferred embodiments the method further comprising independently moving the dispenser and the at least one rotating electrode along the precipitation electrode.

According to still further features in the described preferred embodiments the method further comprising synchronically moving the dispenser and the at least one rotating electrode along the precipitation electrode.

According to still further features in the described preferred embodiments the precipitation electrode comprises at least one rotating mandrel.

According to still further features in the described preferred embodiments the dispenser comprises a mechanism for forming a jet of the is liquefied polymer.

According to still further features in the described preferred embodiments the mechanism for forming a jet of the liquefied polymer includes a dispensing electrode.

According to still further features in the described preferred embodiments the subsidiary electrode is of a shape selected from the group consisting of a plane, a cylinder, a torus and a wire.

According to yet another aspect of the present invention there is provided a tubular structure, comprising at least one layer of electrospun polymer fibers, each layer having a predetermined porosity and an alternating density in a longitudinal direction of the tubular structure.

According to further features in preferred embodiments of the invention described below, the tubular structure is sized and having properties so as to serve as a vascular prosthesis.

According to still another aspect of the present invention there is provided a vascular prosthesis, comprising at least one layer of electrospun polymer fibers, each layer having a predetermined porosity and an alternating density in a longitudinal direction of the vascular prosthesis.

According to further features in preferred embodiments of the invention described below, the polymer is a biocompatible polymer.

According to still further features in the described preferred embodiments the polymer is selected from the group consisting of polyethylene terephtalat and polyurethane.

According to still further features in the described preferred embodiments said at least one layer includes at least one drug incorporated therein, for delivery of the at least one drug into a body vasculature during or after implantation of the vascular prosthesis within the body vasculature.

According to still further features in the described preferred embodiments the electrospun polymer fibers are a combination of a biodegradable polymer and a biostable polymer.

The present invention successfully addresses the shortcomings of the presently known configurations by providing an electrospinning apparatus and method capable of improving kinking resistance of tubular structures produced thereby.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3a is a mechanism for increasing a local density of the polymeric shell embodied as a plurality of rollers, according to the present invention;

FIG. 3b is the mechanism for increasing a local density of the polymeric shell embodied as a spiral pattern, according to the present invention;

FIG. 3c is the mechanism for increasing a local density of the polymeric shell embodied as a rigid irregular pattern, according to the present invention;

FIG. 4 is a schematic illustration of the apparatus for forming a tubular structure further comprising a subsidiary electrode, according to the present invention;

FIG. 7 is a schematic illustration of the intertwining mechanism in the form of at least one rotating electrodes, according to the present invention.

FIG. 8a is a tubular structure having toroidal pattern of high density regions, according to the present invention;

FIG. 8b is a tubular structure having spiral-like pattern of high density regions, according to the present invention; and FIG. 8c is a tubular structure having irregular pattern of high density regions, according to the present invention.

DESCRIPTION OF THE PREFERRED EMBODIMENTS

The present invention is of a method and apparatus for forming a tubular structure which can be for example an artificial blood vessel.

Specifically, the present invention can be used to fabricate a tubular structure having an improved kinking resistance.

Figure 1:
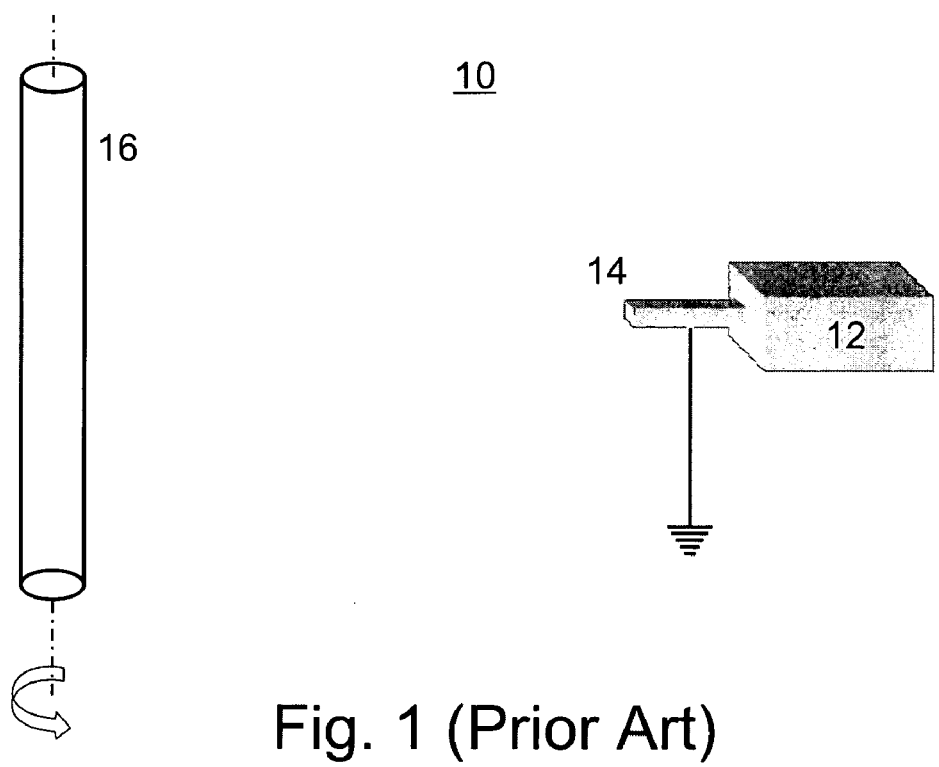
FIG. 1 is a schematic illustration of a prior art electrospinning apparatus.
Figure 2:
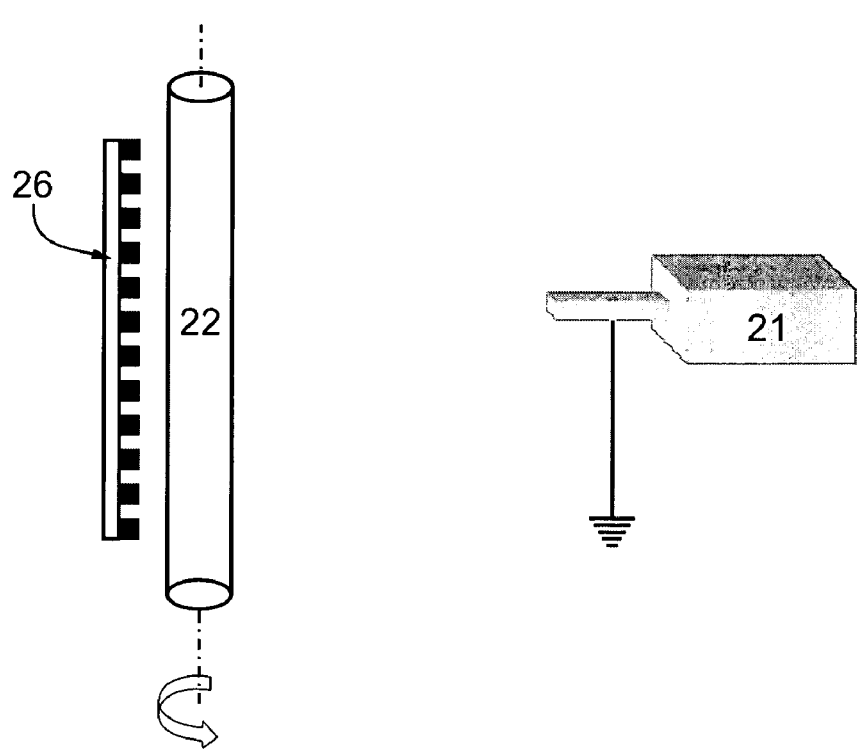
FIG. 2 is a schematic illustration of an apparatus for forming a tubular structure from a liquefied polymer, according to one embodiment of the present invention.

For purposes of better understanding the present invention, as illustrated in FIGS. 2-8 of the drawings, reference is first made to the construction and operation of a conventional (i.e., prior art) electrospinning apparatus as illustrated in FIG. 1.

FIG. 1 illustrates an apparatus for manufacturing a nonwoven material using electrospinning, which is referred to herein as apparatus 10.

Apparatus 10 includes a dispenser 12 which can be, for example, a reservoir provided with one or more capillary apertures 14. Dispenser 12 serves for storing the polymer to be spun in a liquid form, i.e., dissolved or melted. Dispenser 12 is positioned at a predetermined distance from a precipitation electrode 16. Precipitation electrode 16 serves for forming the tubular structure thereupon. Precipitation electrode 16 is typically manufactured in the form of a mandrel or any other substantially cylindrical structure. Precipitation electrode 16 is rotated by a mechanism such that a tubular structure is formed when coated with the polymer. Dispenser 12 is typically grounded, while precipitation electrode 16 is connected to a source of high voltage, preferably of negative polarity, thus forming an electric field between dispenser 12 and precipitation electrode 16. Alternatively, precipitation electrode 16 can be grounded while dispenser 12 is connected to a source of high voltage, preferably with positive polarity.

To generate a tubular structure, a liquefied polymer (e.g., melted polymer or dissolved polymer) is extruded, for example under the action of hydrostatic pressure, or using a pump (not shown in FIG. 1), through capillary apertures 14 of dispenser 12. As soon as meniscus of the extruded liquefied polymer forms, a process of solvent evaporation or cooling starts, which is accompanied by the creation of capsules with a semi-rigid envelope or crust. An electric field, occasionally accompanied by a unipolar corona discharge in the area of dispenser 12, is generated by the potential difference between dispenser 12 and precipitation electrode 16. Because the liquefied polymer possesses a certain degree of electrical conductivity, the above-described capsules become charged. Electric forces of repulsion within the capsules lead to a drastic increase in hydrostatic pressure. The semi-rigid envelopes are stretched, and a number of point micro-ruptures are formed on the surface of each envelope leading to spraying of ultra-thin jets of liquefied polymer from dispenser 12.

Under the effect of a Coulomb force, the jets depart from dispenser 12 and travel towards the opposite polarity electrode, i.e., precipitation electrode 16. Moving with high velocity in the inter-electrode space, the jet cools or solvent therein evaporates, thus forming fibers which are collected on the surface of precipitation electrode 16.

Tubular structure formed in a typical electrospinning process (e.g., as employed by apparatus 10 ), lack sufficient kinking resistance and further reinforcement of the final product is often necessary to support the lumen of the tubular structure while bending. According to the present invention there is provided an apparatus for forming a tubular structure having an intrinsic kinking resistance (i.e. without additional supporting elements).

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now again to the drawings, FIG. 2 illustrates an apparatus, generally referred to herein as apparatus 20, for forming a tubular structure from a liquefied polymer according to the teachings of the present invention. Apparatus 20 includes a dispenser 21 for dispensing the liquefied polymer, and a precipitation electrode 22 being at a first potential relative to dispenser 21. Precipitation electrode 22 serves for generating a polymeric shell thereupon. Apparatus 20 further includes a mechanism 26 for increasing a local density of the polymeric shell in a plurality of predetermined sub-regions of the polymeric shell, thereby to provide a tubular structure having an alternating density in a longitudinal direction.

Dispenser 21 is preferably at a first potential relative to dispenser 21. According to a preferred embodiment of the present invention, dispenser 21 may be operable to move along precipitation electrode 22, so as to ensure complete or predetermined covering of precipitation electrode 22. In addition, precipitation electrode 22 is preferably operable to rotate around a longitudinal axis.

The operations of dispenser 21 and precipitation electrode 22 to form a polymeric shell are similar to the operations of dispenser 12 and precipitation electrode 16 of apparatus 10, as detailed hereinabove. The position and size of, and the material from which mechanism 26 is made of are all selected to ensure that precipitation electrode 22 shields mechanism 26, hence minimize any change in the electric field due to the nearby presence mechanism 26. Mechanism 26 is preferably grounded.

According to a preferred embodiment of the present invention, mechanism 26 may be any device capable of locally increasing the density of the polymer fibers. Specifically, mechanism 26 may be a pressing mechanism, so that the polymer fibers, being pressed by mechanism 26, are efficiently stuck together forming a rigid and denser three-dimensional structure. Such condensation results in a certain reduction of electrical resistance in the condensed area and a corresponding intensification of fiber deposition thereat in subsequent electrospinning steps.

Reference is now made to FIGS. 3*a-c* showing three alternatives for mechanism 26. In FIG. 3*a*, mechanism 26 is embodied as a plurality of rollers 32 spaced apart from one another. Rollers 32 are connected to an axle 34 and operable to freely rotate about axle 34. In FIG. 3*b*, mechanism 26 is embodied as a rigid spiral pattern 36, operable to rotate about a longitudinal axis 38. In FIG. 3*c*, mechanism 26 is embodied as a rigid irregular pattern 37, operable to rotate about a longitudinal axis 38.

In the preferred embodiment in which mechanism 26 is a spiral, longitudinal forces are present between mechanism 26 and precipitation electrode 22. Hence, according to a preferred embodiment of the present invention, mechanism 26 may be operable to move along longitudinal axis 38, so as to prevent smearing of the compressed sub-regions of precipitation electrode 22. It should be understood, that the length of mechanism 26 is chosen so that a predetermined length of the produced tubular shell is in contact with mechanism 26.

The rotation of mechanism 26 may be either free rotation or forced rotation, by the use of a rotating device 39. According to a preferred embodiment of the present invention, mechanism 26 may be either in inactive mode, i.e. detached from precipitation electrode 22, or in active mode i.e. when mechanism 26 (either embodied as rollers 32 or as spiral pattern 36) is pressed against precipitation electrode 22. Whether or not mechanism 26 is connected to rotating device 39, when mechanism 26 is in its active mode, the relative transverse velocity between precipitation electrode 22 and mechanism 26 should be synchronized to substantially zero, so as to ensure a rolling without sliding motion. Once mechanism 26 is pressed onto precipitation electrode 22, denser three dimensional patterns start to appear on the surface of the formed tubular structure, which patterns depend on the shape and size of mechanism 26 as shown in FIGS. 3*a-c*.

Apparatus 20 described hereinabove can be efficiently used for generating tubular structures upon a precipitation electrode having or large radius of curvature. However, when using a precipitation electrode being at least partially with small radius of curvature, the orientation of the electric field maximal strength vector is such that precipitation electrode 22 is coated coaxially by the fibers. Thus, small diameter products, may exhibit limited radial strength.

In cases where precipitation electrode 22 comprises sharp edges and/or variously shaped and sized recesses, the electric field magnitude in the vicinity of precipitation electrode 22 may exceed the air electric strength (about 30 kV/cm), and a corona discharge may develop in the area of precipitation electrode 22. The effect of corona discharge decreases the coating efficiency of the process as further detailed herein.

Corona discharge initiation is accompanied by the generation of a considerable amount of air ions having opposite charge sign with respect to the charged fibers. Since an electric force is directed with respect to the polarity of charges on which it acts, theses ions start to move at the opposite direction to fibers motion i.e., from precipitation electrode 22 towards dispenser 24. Consequently, a portion of these ions generate a volume charge (ion cloud), non-uniformly distributed in the inter-electrode space, thereby causing electric field lines to partially close on the volume charge rather than on precipitation electrode 22. Moreover, the existence of an opposite volume charges in the inter-electrode space, decreases the electric force on the fibers, thus resulting in a large amount of fibers accumulating in the inter-electrode space. Such an effect may lead to a low-efficiency process of fiber coating, and may even result in a total inability of fibers to be collected upon precipitation electrode 22.

The present invention successfully addresses both of the above problems, by providing a subsidiary electrode within apparatus 20, so as to control the electric field. Specifically, a subsidiary electrode may either substantially decreases non-uniformities in the electric field and/or provides for controlled fiber orientation upon deposition.

Reference is now made to FIG. 4, which depicts another preferred embodiment of the present invention, which may be employed for fabricating tubular structures having a small diameter and/or intricate-profile. Hence, apparatus 20 may further comprise a subsidiary electrode 46 which is kept at a second potential difference relative to dispenser 21. Subsidiary electrode 46 serves for controlling the direction and magnitude of the electric field in the inter-electrode space and as such, subsidiary electrode 46 can be used to control the orientation of polymer fibers deposited on precipitation electrode 22. In some embodiments, subsidiary electrode 46 serves as a supplementary screening electrode. Broadly stated, use of screening results in decreasing the coating precipitation factor, which is particularly important upon precipitation electrodes having at least a section of small radii of curvature.

According to a preferred embodiment of the present invention the size, shape, position and number of subsidiary electrode 46 is selected so as to maximize the coating precipitation factor, while minimizing the effect of corona discharge in the area of precipitation electrode 22 and/or so as to provide for controlled fiber bundles orientation upon deposition. Thus, subsidiary electrode 46 may be fabricated in a variety of shapes each serving a specific purpose. Electrode shapes which can be used with apparatus 20 of the present invention include, but are not limited to, a plane, a cylinder, a torus a rod, a knife, an arc or a ring.

According to a presently preferred embodiment of the invention, subsidiary electrode 46 may be operable to move along precipitation electrode 22. Such longitudinal motion may be in use when enhanced control over fiber orientation is required. The longitudinal motion of subsidiary electrode 46 may be either independent or synchronized with the longitudinal motion of dispenser 21. Subsidiary electrode 46 may also be tilted through an angle of 45°-90° with respect to a longitudinal axis of precipitation electrode 22, which tilting may be used to provide for controlled fiber-bundle orientation upon deposition, specifically, large angles result in predominant polar (transverse) orientation of bundles.

Depending on the use of the tubular structure formed by apparatus 20, it may be required to enhance the strength and/or elasticity, both in a radial direction and in an axial direction, of the final product. This is especially important when the tubular structure is to be used in medical applications, where a combination of high elasticity, strength, small thickness, porosity, and low basis weight are required. According to a preferred embodiment of the present invention the strength of the tubular structure may be significantly enhanced, by employing an additional electric field having at least one rotating element, as described herein.

Figure 5:
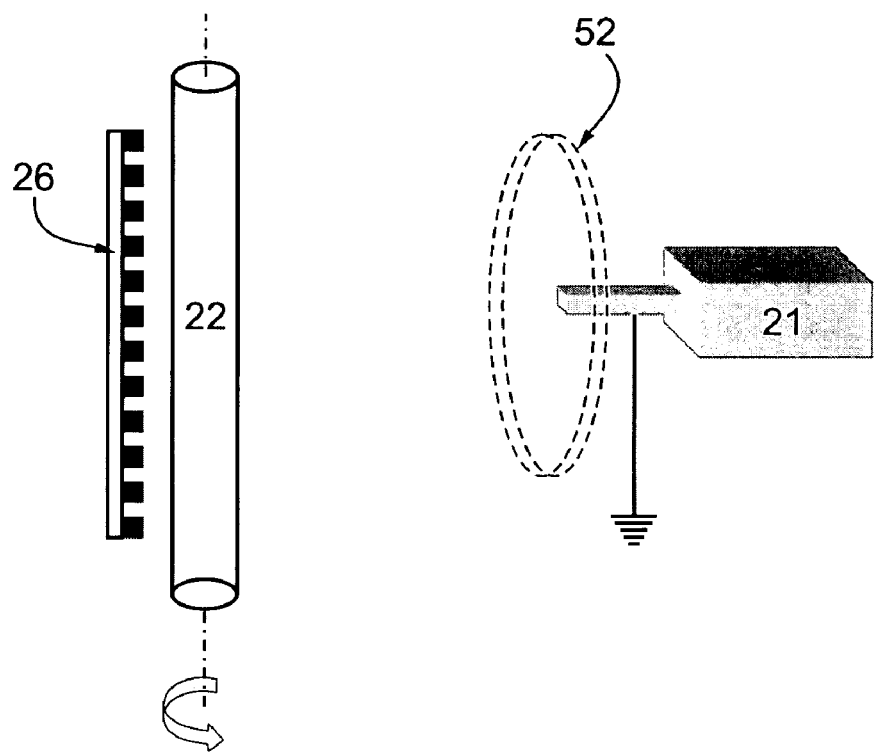
FIG. 5 is a schematic illustration of the apparatus for forming a tubular structure further comprising a mechanism for intertwining at least a portion of the polymer fibers, according to the present invention.

Referring to FIG. 5, apparatus 20 further includes a mechanism 52 for intertwining at least a portion of the polymer fibers, so as to provide at least one polymer fiber bundle moving in a direction of precipitation electrode 22. Mechanism 52 may include any mechanical and/or electronic components which are capable for intertwining the polymer fibers "on the fly", as is further detailed hereinunder, with reference to FIGS. 6-7.

Figure 6:
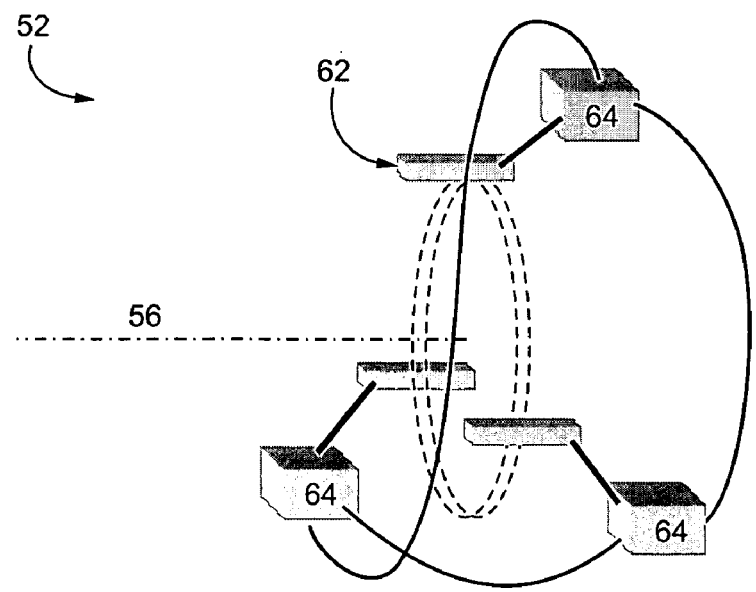
FIG. 6 is a schematic illustration of the intertwining mechanism in the form of a plurality of stationary electrodes, according to the present invention.

Thus, FIG. 6 illustrates one embodiment of the present invention in which mechanism 52 includes a system of electrodes being laterally displaced from dispenser 21 and preferably at a third potential relative to dispenser 21. According to a preferred embodiment of the present invention the system of electrodes may be constructed in any way known in the art for providing an electric field rotating around a first axis 56 defined between said dispenser and said precipitation electrode.

For example, as shown in FIG. 6, the system of electrodes may include two or more stationary electrodes 62, connected to at least one power source 64, so that the potential difference between electrodes 62 and precipitation electrode 22 (and between electrodes 62 and dispenser 21 ) varies in time. Power sources 64, being electronically communicating with each other so as to synchronize a relative phase between electrodes 62. Hence, each of stationary electrodes 62 generates a time-dependent electric field having a constant direction. The electronic communication between power sources 64 ensures that the sum of all (time-dependent) field vectors is rotating around first axis 56.

Reference is now made to FIG. 7, in which mechanism 52 is manufactured as at least one rotating electrode 72, operable to rotate around first axis 56. Rotating electrode 72, being at a third potential relative to dispenser 21, generates an electric field, the direction of which follows the motion of rotating electrode 72, hence an electric field having at least one rotating component is generated.

According to the presently preferred embodiment of the invention, in operation mode of apparatus 20, the liquefied polymer is dispensed by dispenser 24, and then, subjected to the electric field, moves in the inter-electrode space. The electric field in the inter-electrode space has at least one rotating component around first axis 56 (generated by the potential difference between mechanism 52 and precipitation electrode 22 ) and a stationary electric field (generated by the potential difference between dispenser 21 and precipitation electrode 22 ). Hence, in addition to the movement in the direction of precipitation electrode 22, the jets of liquefied polymer, under the effect of the rotating component of the electric field twist around first axis 56. The rotation frequency may be controlled by a suitable choice of configuration for the system of electrodes, as well as on the value of the potential differences employed.

At a given time, the effect of the rotating component of the electric field on the jets neighboring mechanism 52 is larger than the effect on the jets which are located far from mechanism 52. Hence, the trajectories of the fibers start crossing one another, resulting in physical contacts and entanglement between fibers prior to precipitation.

Thus, apparatus 20 generates higher-order formations of fiber bundles from the elementary fibers in the spray jet. The structure of the formed fiber bundles is inhomogeneous and depends on the distance of the fiber bundle from mechanism 52. Specifically, the extent of fiber twisting and interweaving, and the amount of fibers in the bundle, is an increasing function of the distance from mechanism 52. During the motion of the bundles in the inter-electrode space, they may also intertwine with one another, forming yet thicker bundles.

The bundles, while formed, continue to move in the inter-electrode space, directed to precipitation electrode 22, forming the tubular structure thereupon. The formed material has three-dimensional reticular structure, characterized by a large number of sliding contacts between fibers. Such contacts significantly increase the strength of the material, due to friction forces between fibers. The ability of fibers for mutual displacement increases the elasticity of the non-woven material under loading.

According to another aspect of the present invention there is provided a method for of forming a tubular structure from a liquefied polymer. The method comprises the following steps which may be executed, for example, using apparatus 20. Hence, in a first step, the liquefied polymer is dispensed via electrospinning from a dispenser in a direction of a precipitation electrode, thus forming a plurality of polymer fibers precipitated onto the precipitation electrode, hence providing a polymeric shell. In a second step, a local density of the polymeric shell is increased in a plurality of predetermined sub-regions of the polymeric shell. These steps may be subsequent or be implemented substantially simultaneously.

According to a preferred embodiment of the present invention, the method may further comprise the step of entangling at least a portion of the polymer fibers, so as to provide at least one polymer fiber bundle moving in the direction of the precipitation electrode. In addition, the method may further comprise a step of controlling fiber and/or fiber bundles orientation of the tubular structure formed upon the precipitation electrode. Still in addition, the method may comprise reducing undesired non-uniformities in the electric field in the vicinity of the precipitation electrode. The steps of controlling fiber and/or fiber bundles orientation and of reducing non-uniformities in the electric field may be performed by the use of a subsidiary electrode, as detailed hereinabove, with reference to FIG. 4.

It is to be understood, that the second step of the invention is performed, whether or not the above additional steps of entangling, controlling fiber orientation and reducing electric field non-uniformities have been employed. Furthermore, each of the additional steps may be employed independently.

According to a preferred embodiment of the present invention, the method may iteratively proceed, so that a multilayer tubular structure is formed. Specifically, once a first layer is formed on the precipitation electrode, the second step of the method is employed so that the first layer of the tubular structure is characterized by an alternating density in a longitudinal direction. The second step may be employed, by switching mechanism 26 into active mode, e.g., by moving axle 34 closer to the precipitation electrode so that rollers 32 are pressed onto the first layer.

In a subsequent iteration, mechanism 26 is switched into an inactive mode (e.g., by moving axle 34 sufficiently far from the precipitation electrode) and the electrospinning step is repeated to provide an additional layer.

Thus, a multilayer structure is formed, wherein each layer is provided with a plurality of higher density sections. Reference is now made to FIGS. 8*a-c*, showing three alternatives of the higher density patterns formed on a specific layer (for example the first layer) of tubular structure 82. Hence, FIG. 8*a* illustrates toroidal high density patterns formed on tubular structure 82. Such high density patterns may be provided for example by using a plurality of rollers as the mechanism for increasing a local density, as detailed hereinabove, and illustrated in FIG. 3*a*. FIG. 8*b* illustrates a high density pattern which may be formed by using spiral pattern as a pressing mechanism, as detailed hereinabove, and illustrated in FIG. 3*b*. Finally, FIG. 3*c* illustrates an irregular pattern of high density formed onto the surface of tubular structure 82, which may be patterned by a pressing mechanism shown and in FIG. 3*c* and described hereinabove.

It should be appreciated that the high density regions on the outer surface the layers of tubular structure 82, may have any predetermined pattern (depending on the application in which tubular structure 82 is to be used), and are not limited to those shown in FIGS. 8*a-c*.

The tubular structure, which may serve in variety of industrial and medical application, is capable to withstand kinking collapse while maintaining a predetermined porosity as well as inner and/or outer surface smoothness. A typical width of the toroidal sections may range from 0.5 to 3 mm.

According to a preferred embodiment of the present invention, the multilayer structure may be sized and having properties so as to serve as a vascular prosthesis. One advantage of a vascular prosthesis, fabricated in accordance to a preferred embodiment of the present invention, is that drug delivery into a body vasculature can be performed during or after implantation of the vascular prosthesis within the body vasculature. Thus, each the layers may incorporate at least one drug therein, for delivery into body vasculature by, for example, a slow release mechanism. It is appreciated that the drug incorporated, as well as the concentration and method of incorporation into the prosthesis is in accordance with the type of vessel being replaced, and with the particular pathology of the patient.

According to a preferred embodiment of the present invention, the liquefied polymer loaded into dispenser 21 may be, for example polyurethane, polyester, polyolefin, polymethylmethacrylate, polyvinyl aromatic, polyvinyl ester, polyamide, polyimide, polyether, polycarbonate, polyacrilonitrile, polyvinyl pyrrolidone, polyethylene oxide, poly (L-lactic acid), poly (lactide-CD-glycoside), polycaprolactone, polyphosphate ester, poly (glycolic acid), poly (DL-lactic acid), and some copolymers. Biolmolecules such as DNA, silk, chitozan and cellulose may also be used in mix with synthetic polymers. Improved charging of the polymer may also be required. Improved charging is effected according to the present invention by mixing the liquefied polymer with a charge control agent (e.g., a dipolar additive) to form, for example, a polymerdipolar additive complex which apparently better interacts with ionized air molecules formed under the influence of the electric field. The charge control agent is typically added in the grams equivalent per liter range, say, in the range of from about 0.001 N to about 0.1 N, depending on the respective molecular weights of the polymer and the charge control agent used.

U.S. Pat. Nos. 5,726,107; 5,554,722; and 5,558,809 teach the use of charge control agents in combination with polycondensation processes in the production of electret fibers, which are fibers characterized in a permanent electric charge, using melt spinning and other processes devoid of the use of a precipitation electrode. A charge control agent is added in such a way that it is incorporated into the melted or partially melted fibers and remains incorporated therein to provide the fibers with electrostatic charge which is not dissipating for prolonged time periods, say weeks or months. In a preferred embodiment of the present invention, the charge control agent transiently binds to the outer surface of the fibers and therefore the charge dissipates shortly thereafter. This is because polycondensation is not exercised at all such that the chemical interaction between the agent and the polymer is absent, and further due to the low concentration of charge control agent employed. The resulting tubular structure is therefore, if so desired, substantially charge free.

Suitable charge control agents include, but are not limited to, mono- and poly-cyclic radicals that can bind to the polymer molecule via, for example, —C=C—, =C—SH— or —CO—NH— groups, including biscationic amides, phenol and uryl sulfide derivatives, metal complex compounds, triphenylmethanes, dimethylmidazole and ethoxytrimethylsians.

Additional objects, advantages, and novel features of the present invention will become apparent to one ordinarily skilled in the art upon examination of the following example, which is not intended to be limiting. Additionally, each of the various embodiments and aspects of the present invention as delineated hereinabove and as claimed in the claims section below finds experimental support in the following example.

EXAMPLE

Reference is now made to the following example, which together with the above descriptions, illustrate the invention in a non limiting fashion.

Tubular structures, 6 mm in diameter and 200 mm in length were manufactured.

A polyurethane of Carbotan 3595 blend was purchased from The Polymer Technology Group Incorporated. This polymer was provided with aromatic urethane hard segment, polycarbonate and silicone co-soft segments and surface-modifying end groups. Silicone-urethane copolymers demonstrate a combination of high mechanical properties with oxidative stability, low rate of hydrolytic degradation biostabillity and tromboresistance. In addition, this polymer is characterized by a high fiber forming ability.

A rod, 6 mm in diameter and 300 mm in length was used as a precipitation electrode, and its central 200 mm portion was coated at ambient temperature (24° C.). The precipitation electrode was rotated at an angular velocity of 100 rpm.

A spinneret was used as the dispensing electrode, the inner diameter of the spinneret was 0.5 mm, and the flow-rate was 3 ml/h. The dispensing electrode was grounded while the precipitation electrode was kept at a potential of −50 kV, relative to the dispensing electrode.

The dispensing electrode was positioned 35 cm from the precipitation electrode. Reciprocal motion of the dispensing electrode was enabled along the mandrel longitudinal axis at a frequency of 5 motions per minute.

An axel connected to a plurality of rollers, spaced apart from one another, was used as a mechanism for increasing a local density. The spacing between the rollers was 1.2 mm, and the width of each roller was 0.8 mm.

Four tubular structures were manufactured according to the teaching of the present invention, for each tubular structure a different pressure of the rollers onto the mandrel was applied. The resulting thicknesses of the compressed sub-regions were: 0.5, 0.6, 0.8 and 0.9. In addition, for comparison, a tubular structure was manufactured employing conventional electrospinning process without the step of increasing local densities.

In all the experiments, the parameters of the electrospinning process were identical, except for the pressure of the rollers on the mandrel.

The manufactured tubular structures were subjected to bending tests so as to compare the kinking resistance of the final product, as a function of the of the compressed sub-regions thicknesses. In addition, global and local measurements of the basis weight were performed for each of the tubular structures.

Table 1 lists some comparative characteristics of the tubular structures produced by a conventional electrospinning technique by the teachings of the present invention.

TABLE 1

| Wall thickness [mm] | | | Basis weight [g/m$^2$] | | Critical |
|---|---|---|---|---|---|
| Compressed sub-region | Non-compressed sub-region | Web | Compressed sub-region | Non-compressed sub-region | bending radius [mm] |
| — | 0.6 | 150 | — | — | 25.0 |
| 0.5 | 0.6 | 200 | 250 | 160 | 7.0 |
| 0.6 | 0.6 | 290 | 430 | 150 | 14.0 |
| 0.8 | 0.6 | 280 | 400 | 150 | 17.0 |
| 0.9 | 0.8 | 420 | 650 | 220 | 11.0 |

As can be seen from Table 1, the existence of compressed sub-regions on the wall of the tubular structure provides relatively heavy sub-regions of the structure. In some experiments, intensification of fiber deposition upon the precipitation electrode in the compressed sub-regions has been observed. This is shown at the bottommost two rows of Table 1, where the wall thickness at the compressed sub-regions is larger than the "original" wall thickness (i.e. at the non-compressed sub-regions). The observed phenomenon is due to a reduction of electrical resistance in the compressed sub-regions.

These compressed sub-regions, significantly increase the ability of the structure to bend. The thinner the thickness of the wall at the compressed subregion, the larger is the kinking resistance of the structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for forming a tubular structure having improved kinking resistance from a liquefied polymer, the apparatus comprising:
   (a) a dispenser for dispensing the liquefied polymer;
   (b) a precipitation electrode being at a first potential relative to said dispenser, said precipitation electrode being designed and constructed for generating a fibrous polymeric shell thereupon; and
   (c) a pressing mechanism for increasing a local density of said polymeric shell in a plurality of predetermined sub-regions of said polymeric shell, thereby to provide a tubular structure having an alternating density in a longitudinal direction, wherein the alternating density regions formed comprises compressed sub-regions and non-compressed sub-regions in a longitudinal direction of the tubular structure, wherein a basis weight of said compressed sub-regions is larger than a basis weight of said non-compressed sub-regions.

2. The apparatus of claim 1, wherein said pressing mechanism for increasing said local density comprises a plurality of rollers spaced apart from one another.

3. The apparatus of claim 1, wherein said pressing mechanism for increasing said local density comprises a spiral pattern.

4. The apparatus of claim 1, wherein said pressing mechanism for increasing said local density comprises a rigid irregular pattern.

5. The apparatus of claim 1, wherein said precipitation electrode comprises at least one rotating mandrel.

6. The apparatus of claim 1, wherein said dispenser is operable to move along said precipitation electrode.

7. The apparatus of claim 3, wherein said dispenser comprises a mechanism for forming a jet of the liquefied polymer.

8. The apparatus of claim 7, wherein said mechanism for forming a jet of the liquefied polymer includes a dispensing electrode.

9. The apparatus of claim 1, further comprising a reservoir for holding the liquefied polymer.

10. The apparatus of claim 1, further comprising a subsidiary electrode being at a second potential relative to said dispenser, and being for modifying an electric field generated between said precipitation electrode and said dispenser.

11. The apparatus of claim 10, wherein said subsidiary electrode serves for reducing non-uniformities in said electric field.

12. The apparatus of claim 10, wherein said subsidiary electrode serves for controlling fiber orientation of the tubular structure formed upon said precipitation electrode.

13. The apparatus of claim 10, wherein said subsidiary electrode is of a shape selected from the group consisting of a plane, a cylinder, a torus and a wire.

14. The apparatus of claim 10, wherein said subsidiary electrode is operative to move along said precipitation electrode.

15. The apparatus of claim 10, wherein said subsidiary electrode is tilted at angle with respect to said precipitation electrode.

16. An apparatus for forming a tubular structure having improved kinking resistance from a liquefied polymer, the apparatus comprising:
   (a) a dispenser for dispensing the liquefied polymer;
   (b) a precipitation electrode being at a first potential relative to said dispenser, said precipitation electrode being designed and constructed for generating a fibrous polymeric shell thereupon;
   (c) a pressing mechanism for increasing a local density of said polymeric shell in a plurality of predetermined sub-regions of said polymeric shell, thereby to provide a tubular structure having an alternating density in a longitudinal direction; wherein the alternating density regions formed comprises compressed sub-regions and non-compressed sub-regions in a longitudinal direction of the tubular structure, wherein a basis weight of said compressed sub-regions is larger than a basis weight of said non-compressed sub-regions and
   (d) a system of electrodes, being laterally displaced from said dispenser, being at a third potential relative to said dispenser and capable of providing an electric field having at least one rotating component around a first axis defined between said dispenser and said precipitation electrode, for intertwining at least a portion of a plurality of polymer fibers dispensed by said dispenser, so as to provide at least one polymer fiber bundle moving in a direction of said precipitation electrode.

17. A method of forming a tubular structure having improved kinking resistance from a liquefied polymer, the method comprising:
   (a) via electrospinning, dispensing the liquefied polymer from a dispenser in a direction of a precipitation electrode, hence forming fibrous polymeric shell; and
   (b) applying pressure onto predetermined sub-regions of said polymeric shell such as to increase a local density of said polymeric shell in said plurality of predetermined sub-regions,
   thereby providing a tubular structure having an alternating density in a longitudinal direction (b), wherein the alternating density regions formed comprises compressed sub-regions and non-compressed sub-regions in a longitudinal direction of the tubular structure, wherein a basis weight of said compressed sub-regions is larger than a basis weight of said non-compressed sub-regions.

18. A tubular structure having improved kinking resistance, comprising at least one layer of electrospun polymer fibers, each layer having a predetermined porosity and an alternating density characterized by compressed sub-regions and non-compressed sub-regions in a longitudinal direction of the tubular structure, wherein a basis weight of said compressed sub-regions is larger than a basis weight of said non-compressed sub-regions.

19. The apparatus of claim 16, wherein said mechanism for increasing said local density comprises a plurality of rollers spaced apart from one another.

20. The apparatus of claim 16, wherein said mechanism for increasing said local density comprises a spiral pattern.

21. The apparatus of claim 16, wherein said mechanism for increasing said local density comprises a rigid irregular pattern.

22. The apparatus of claim 16, further comprising a subsidiary electrode being at a second potential relative to said dispenser, and being for modifying an electric field generated between said precipitation electrode and said dispenser.

23. The apparatus of claim 22, wherein said subsidiary electrode serves for reducing non-uniformities in said electric field.

24. The apparatus of claim 22, wherein said subsidiary electrode serves for controlling fiber orientation of the tubular structure formed upon said precipitation electrode.

25. The apparatus of claim 22, wherein said subsidiary electrode is of a shape selected from the group consisting of a plane, a cylinder, a torus and a wire.

26. The apparatus of claim 22, wherein said subsidiary electrode is operative to move along said precipitation electrode.

27. The apparatus of claim 22, wherein said subsidiary electrode is tilted at angle with respect to said precipitation electrode.

28. The method of claim 17, further comprising independently repeating said steps (a) and (b) at least once.

29. The method of claim 17, wherein said increasing said local density is done by pressing a plurality of rollers, spaced apart from one another, onto said polymeric shell.

30. The method of claim 17, wherein said increasing said local density is done by pressing a spiral pattern onto said polymeric shell.

31. The method of claim 17, wherein said increasing said local density is done by pressing a rigid irregular pattern onto said polymeric shell.

32. The method of claim 17, further comprising reducing non-uniformities in an electric field generated between said precipitation electrode and said dispenser.

33. The method of claim 32, wherein said reducing non-uniformities in said electric field is done by positioning a subsidiary electrode close to said precipitation electrode.

34. The method of claim 17, further comprising controlling fiber orientation of the tubular structure formed upon said precipitation electrode.

35. The method of claim 34, wherein said controlling fiber orientation is done by positioning a subsidiary electrode close to said precipitation electrode.

36. The tubular structure of claim 18, capable of withstanding kinking collapse when bent at a bending radius which is lower than 25 mm.

37. The tubular structure of claim 18, wherein said basis weight of said compressed sub-regions is at least 250 $g/m^2$ and said basis weight of said non-compressed sub-regions is not higher than 220 $g/m^2$.

* * * * *